United States Patent [19]

Hagen et al.

[11] Patent Number: 4,817,414
[45] Date of Patent: Apr. 4, 1989

[54] MEASURING ARRANGEMENT FOR DETECTING THE LEVEL OF COMBUSTIBLE GASES MIXED WITH AIR

[75] Inventors: Werner Hagen; Claus-Dieter Brandt, both of Bad Schwartau; Gerd Mahrt, Barnitz, all of Fed. Rep. of Germany

[73] Assignee: Drägerwerk Aktiengesellschaft, Lübeck, Fed. Rep. of Germany

[21] Appl. No.: 68,905

[22] Filed: Jun. 30, 1987

[30] Foreign Application Priority Data

Jul. 3, 1986 [DE] Fed. Rep. of Germany ....... 3622307

[51] Int. Cl.$^4$ ............................................ G01N 27/12
[52] U.S. Cl. ..................................................... 73/25
[58] Field of Search .......................... 73/25, 26, 27, 23; 422/94, 95, 96, 98; 338/34

[56] References Cited

U.S. PATENT DOCUMENTS

| 3,091,957 | 6/1963 | Hampton | 73/27 R |
| 3,519,391 | 7/1970 | Winter et al. | 73/27 R |
| 4,498,330 | 2/1985 | Hosoya | 73/23 |
| 4,571,543 | 2/1986 | Raymond et al. | 324/425 |
| 4,572,900 | 2/1986 | Wohltjen | 73/23 |

FOREIGN PATENT DOCUMENTS

| 1648857 | 1/1971 | Fed. Rep. of Germany . | |
| 1698549 | 11/1971 | Fed. Rep. of Germany . | |
| 3127431 | 2/1983 | Fed. Rep. of Germany . | |
| 2456950 | 1/1981 | France | 73/27 R |
| 2103806 | 2/1983 | United Kingdom | 73/2.5 |
| 2165948 | 4/1986 | United Kingdom | 73/23 |

Primary Examiner—John Chapman
Assistant Examiner—Hezron E. Williams
Attorney, Agent, or Firm—Walter Ottesen

[57] ABSTRACT

A measuring arrangement for detecting the level of combustible gases mixed with air such as methane in air includes a measuring sensor responsive to the heat-conductivity of the proportion of the gas to be detected. The effect of the ambient temperature on the heat-conductivity measurement is eliminated through a simple circuit configuration consuming low power for a measurement of heat-conductivity alone as well as for such a measurement in combination with a reaction-heat measurement. For this purpose, the heat-conductivity sensor is connected to a constant-current source. A measuring takeoff circuit for the heat conductivity is connected in parallel to the heat-conductivity sensor and is provided in the form of a series circuit including a measuring signal terminal and a compensating voltage source. The compensating voltage source generates a compensating voltage which changes in magnitude and direction in correspondence with the temperature-dependent change in the voltage drop across the heat-conductivity sensor.

6 Claims, 1 Drawing Sheet

MEASURING ARRANGEMENT FOR DETECTING THE LEVEL OF COMBUSTIBLE GASES MIXED WITH AIR

FIELD OF THE INVENTION

The invention relates to a measuring apparatus for detecting the level of combustible gases mixed with air, especially of methane in air, which includes a sensor responsive to the heat conductivity of the gas concentration to be detected.

BACKGROUND OF THE INVENTION

Published German Patent Application DE-OS No. 16 98 549 discloses a measuring apparatus of this type wherein a sensor for the heat conductivity and a sensor for the reaction heat of the gas components to be detected are arranged in the bridge branches of a measuring bridge. At low concentrations of the combustible gas, the reaction-heat effect exceeds the heat-conductivity effect, so that with increasing concentration of the combustible gas, also an increasing measuring signal can be tapped in the diagonal branch or measuring branch of the measuring bridge. With a further increase of the concentration of the combustible gas in air, the reaction-heat effect, because of the further decreasing oxygen concentration in the mixture, becomes smaller, and the effect of heat conductivity on the unbalancing of the measuring bridge increases. Depending on the balancing of the individual bridge branches with respect to one another, the measuring apparatus will be switched to full amplitude in the measuring branch starting at a predetermined heat-conductivity signal and thereby showing that the concentration of combustible gas mixed with air is above a predetermined limit. Thus, to that extent, a clear indication is obtained; otherwise, a decline of the reaction-heat signal with a further increasing concentration of the combustible gas would falsely indicate harmlessly low concentrations to the user of such known apparatus.

However, with the known measuring apparatus, it is not possible to measure the true content of the combustible gases mixed with air when a predetermined limit value for the reaction-heat measurement is exceeded.

German Published Patent Application DE-OS No. 31 27 431 discloses a monitoring instrument for the concentrations of combustible gases which considers the foregoing and suggests connecting a first bridge circuit for measuring the reaction heat in series with a second bridge circuit having its own compensation resistance which is designed exclusively for the utilization of the heat conductivity.

Doubling the number of measuring bridges is, however, expensive and doubles the complexity of the circuit and increases energy consumption.

A katharometer is disclosed in German Published Patent Application DE-OS No. 16 48 857 for detecting the level of combustible gases by measuring heat conductivity. This katharometer includes a measuring bridge in which a first sensor branch utilizes a heating filament as a heat-conductivity sensor exposed to the gas to be measured and a second sensor branch utilizes an encapsulated heating filament of the same kind for compensating for the effect of the changing ambient temperature. The indicating instrument is in the diagonal of the bridge. A disadvantage here is the high power requirement of the compensating element maintained at elevated temperature in the same way as the actual measuring sensor.

SUMMARY OF THE INVENTION

In contrast to the foregoing, it is an object of the invention to provide a measuring apparatus for detecting the level of combustible gases mixed with air wherein simple circuit means consuming low power are utilized to exclude the influence of ambient temperature on the measurement of heat conductivity when heat conductivity alone is measured as well as in combination with the measurement of heat reaction.

According to a feature of the invention, the heat-conductivity sensor is connected to a source of constant current and a measuring tap is provided in parallel with the sensor for the heat conductivity. The measuring tap is configured as a series circuit comprising a measuring signal terminal and a source of compensating voltage. The magnitude of this compensating voltage is changeable in the same direction as the temperature-dependent voltage-drop change across the heat-conductivity sensor and, according to the polarity, is opposed to this voltage-drop change.

Since the heat-conductivity sensor is traversed by constant current, the voltage drop across this sensor is only dependent on the parameters of heat conductivity and ambient temperature. The temperature dependence is eliminated by means of the source of compensating voltage. In this way, the temperature-compensated signal which can be tapped or taken off at the measuring-signal terminal means is alone a measure of the heat conductivity.

It thus is possible to perform a heat-conductivity measurement with a low power requirement because it is not necessary, as in the case of the known measuring instrument, to provide a second sensor for temperature compensation in a measuring bridge, the second sensor having a high power requirement and being connected in parallel with the first heat-conductivity sensor and shielded in a capsule from the combustible gas to be detected.

On the assumption that signal decoupling at the measuring signal terminal means requires no power, it also is possible to produce a compensating voltage with the compensation voltage source under conditions of the lowest power requirements. This has a particularly favorable effect on portable equipment. At the same time, the compensating voltage can in general be produced by passing current through passive components or also by passing current through active members such as a thermoelement, for example, which produce a temperature-dependent compensating voltage. In contrast to the known measuring equipment, it is no longer necessary to provide additional encapsulated compensating resistors which are otherwise similar to conductivity sensors and which, in addition, consume a large amount of power.

In a particularly simple manner, the compensating voltage source can comprise a compensating-constant current source, to which an adjustable temperature measuring sensor is connected in parallel. The temperature measuring sensor is advantageously arranged in the vicinity of the heat-conductivity sensor and has the same temperature characteristic as the heat-conductivity sensor at constant current flow. For better adaptation, the resistance of the temperature measuring sensor can be adjustable.

A particularly simple adjustment or trimming is achieved by providing a temperature-independent, variable dropping resistor connected ahead of the temperature-measuring sensor. By suitable selection of the current intensity of the compensating-constant current source and of the dropping resistor, an adequate temperature compensation of the changes in the voltage drop across the heat-conductivity sensor can be achieved since a linear temperature characteristic curve can be assumed.

A measuring apparatus for detecting the level of combustible gases mixed with air can also render the heat conductivity signal measurable in that the measuring signal terminal means is connected via the heat-conductivity sensor to a signal-processing device. A temperature sensor is connected to this device by means of which it takes into consideration the temperature dependence of the heat-conductivity signal and corrects this signal with respect to the temperature. In this manner, a low power temperature-independent measurement of the heat conductivity is made possible, for which no additional encapsulated comparison sensor for temperature compensation is required.

According to a preferred embodiment of the invention, the signal processing device contains a multiplexer, which alternately requests the diagonal branch of the measuring bridge for the reaction-heat measurement and upon exceeding a limit value, picks up the heat-conductivity signal together with the temperature associated therewith, and supplies all the signals via an analog-to-digital converter to a microprocessor. In the microprocessor, the temperature characteristic curve is stored, so that each heat-conductivity signal is shown corrected or can be further processed.

A combined measurement of reaction heat and heat conductivity of a combustible gas with the aid of a measuring bridge achieves the result that a more accurate reaction heat measurement can be performed in the lower concentration region, which in a higher concentration region such as starting with the lower explosion limit, is separated from the heat-conductivity measurement, so that an unambiguous correlation of the gas concentration and measuring signal is possible. Moreover, the heat-conductivity signal is independent of the ambient temperature because of the compensation circuit.

The comparison resistances in the measuring bridge are selected to be of such high ohmic value that a virtually constant current flows through the measuring sensors. The measuring signal for the reaction heat can be tapped from the diagonal branch and the portion of the heat conductivity in the reaction-heat signal is eliminated by means of the heat conductivity sensor.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
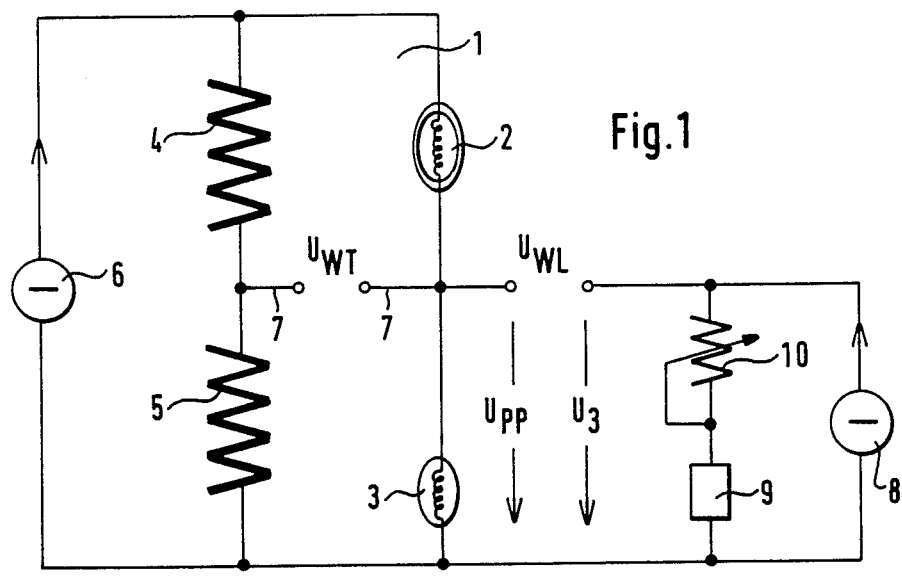
FIG. 1 is a schematic of an embodiment of the measuring apparatus of the invention which includes a bridge circuit for the heat conductivity and reaction heat measurement and a source of compensating voltage for the measurement of heat conductivity; and, FIG. 2 is another embodiment of the measuring apparatus of the invention showing the bridge circuit of FIG. 1 in combination with a computing device for signal processing.

FIG. 1 shows a measuring bridge 1 which includes a catalytically operating reaction-heat sensor 2 and a heat-conductivity sensor 3 with the corresponding compensating resistors 4, 5. The measuring bridge 1 is supplied by a constant-current source 6. The reaction-heat signal $U_{WT}$ can be tapped at the diagonal branch 7 of the measuring bridge. Measuring-signal terminal means for taking off voltage signal $U_{WL}$ and a source of compensating voltage conjointly define a series current which is connected in parallel with the heat-conductivity sensor 3. The compensating-voltage source includes a compensating constant-current source 8 and a temperature-measuring sensor 9 connected in parallel therewith. A temperature-independent trimming resistor 10 is connected in series with temperature measuring sensor 9. The temperature-dependent voltage drop $U_3$ across the temperature-measuring sensor 9 and trimming resistor 10 corresponds to the temperature-dependent portion of the voltage drop $U_{PP}$ across the heat-conductivity sensor 3 when the trimming resistor 10 is appropriately trimmed and the current intensity of the compensating constant-current source 8 is correspondingly set. The voltage drop $U_3$ eliminates this temperature-dependent portion of voltage drop $U_{PP}$ because of its opposite polarity. In this manner, a temperature-independent voltage signal $U_{WL}$ can be tapped from the measuring signal terminal means.

Figure 2:
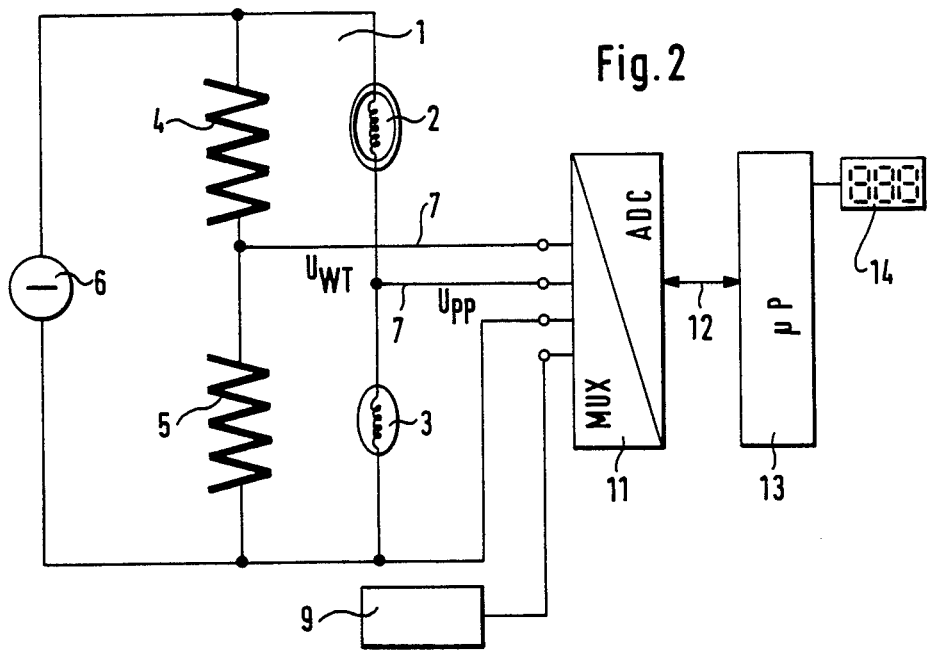

In FIG. 2, the measuring bridge 1 of FIG. 1 is connected at its diagonal branch 7 to a multiplexer unit 11 which includes a multiplexer and an analog-to-digital converter connected to the latter. The multiplexer unit 11 is also connected to the heat-conductivity sensor 3 and to the temperature-measuring sensor 9. The signals processed in this manner are transmitted via a transmission line 12 to a microprocessor 13 which also controls the functions of the multiplexer and of the analog-to-digital converter contained in the multiplexer unit 11. These signals are indicated as a measured value by an indicator unit 14, for example, after the measuring signals are corrected using the temperature characteristic curve of the heat-conductivity sensor 3 stored in the microprocessor 13.

An instrument for measuring the heat conductivity alone would correspond to FIGS. 1 and 2 with the modification that the reaction-heat measuring sensor 2, the compensating resistors 4, 5 and the diagonal branch 7 are omitted and the constant-current source 6 is connected directly to both terminals of the heat-conductivity sensor 3.

It is understood that the foregoing description is that of the preferred embodiments of the invention and that various changes and modifications may be made thereto without departing from the spirit and scope of the invention as defined in the appended claims.

What is claimed is:

1. A measuring arrangement for detecting the proportion of a combustible gas mixed with air such as methane in air, the measuring arrangement comprising:

constant-current supply means for supplying a constant current;

a heat-conductivity measuring sensor for responding to the heat conductivity of the proportion of gas to be detected, said heat-conductivity measuring sensor being connected to said supply means for receiving said constant current with a voltage drop occurring across said measuring sensor that changes in dependence upon temperature;

measuring signal terminal means for taking off a measuring voltage signal;

compensating voltage source means for generating a compensating voltage which changes in magnitude and direction in correspondence with the temperature-dependent changes in said voltage drop;

said measuring signal terminal means and said compensating voltage source means conjointly defining a series circuit connected in parallel with said measuring sensor; and, said compensating voltage source means being connected into said series circuit so as to cause said compensating voltage to act in opposition to said temperature-dependent changes in said voltage drop whereby said measuring voltage signal is independent of changes in temperature and is exclusively indicative of said heat conductivity.

2. The measuring arrangement of claim 1, wherein said compensating voltage source means comprises a compensating constant-current source and a trimmable temperature-measuring sensor connected in parallel with said constant-current source.

3. The measuring arrangement of claim 2, wherein said compensating voltage source means further comprises a trimmable, temperature-independent, dropping resistor connected in series with said temperature-measuring sensor.

4. The measuring arrangement of claim 1, comprising: a measuring bridge connected to said constant-current source, said measuring bridge having a first measuring branch containing said heat-conductivity measuring sensor and a second measuring branch containing a reaction-heat sensor for responding to the reaction heat of the combustible gas.

5. A measuring arrangement for detecting the portion of a combustible gas mixed with air such as methane in air, the measuring arrangement comprising:

supply means for supplying a current;

a heat-conductivity measuring sensor for responding to the heat conductivity of the proportion of gas to be detected, said measuring sensor having a temperature characteristic curve and being connected to said supply means for receiving said current and providing a first signal indicative of said heat conductivity, said signal being influenced by temperature;

temperature-measuring sensor for providing a second signal indicative of temperature;

signal processing means connected to said heat-conductivity measuring sensor and also to said temperature-measuring sensor for correcting the influence on said first signal by the temperature; and, said signal processing means including: a multiplexer unit having a multiplexer for receiving said first and second signals and an analog-to-digital convertor; and, microprocessor connected to the output of said convertor, the microprocessor including: storage means for storing the temperature characteristic curve of said heat-conductivity measuring sensor; and, correction means for correcting said signals using said temperature characteristic curve.

6. The measuring arrangement of claim 5, comprising:

a measuring bridge having a first measuring branch containing said heat-conductivity measuring sensor and a second measuring branch containing a reaction-heat sensor for responding to the reaction heat of the combustible gas; and, constant-current source means for supplying a constant current to said measuring bridge.

* * * * *